United States Patent [19]

Noiles

[11] Patent Number: 4,662,891
[45] Date of Patent: May 5, 1987

[54] FIXATION ELEMENTS FOR ARTIFICIAL JOINTS

[75] Inventor: Douglas G. Noiles, New Canaan, Conn.

[73] Assignee: Joint Medical Products Corporation, Stamford, Conn.

[21] Appl. No.: 553,519

[22] Filed: Nov. 21, 1983

[51] Int. Cl.⁴ .............................. A61F 2/34
[52] U.S. Cl. ........................ 623/22; 623/16; 128/92 R; 128/92 VJ; 128/92 VV
[58] Field of Search ............... 3/1.912, 1, 1.9, 1.91, 3/1.911, 1.913; 128/92 E, 92 CA, 92 R, 305, 92 XJ; 433/174; 408/215; 10/140, 141 R

[56] References Cited
U.S. PATENT DOCUMENTS

| 1,288,893 | 12/1918 | Holmes | 10/140 X |
| 2,696,817 | 12/1954 | Prevo | 3/1.91 X |
| 3,044,341 | 7/1962 | Stern | 10/140 X |
| 4,116,200 | 9/1978 | Braun et al. | 128/92 E X |
| 4,262,369 | 4/1981 | Roux | 3/1.912 |
| 4,404,691 | 9/1983 | Buning et al. | 128/92 C X |
| 4,433,686 | 2/1984 | Charnley | 128/92 C X |

FOREIGN PATENT DOCUMENTS

| 2645101 | 4/1976 | Fed. Rep. of Germany ... 3/1.912 X |
| 523654 | 4/1955 | Italy | 10/140 |
| 83/02555 | 8/1983 | PCT Int'l Appl. | 623/23 |
| 83/00089 | 8/1983 | PCT Int'l Appl. | |

Primary Examiner—Richard J. Apley
Assistant Examiner—Alan W. Cannon
Attorney, Agent, or Firm—Maurice M. Klee

[57] ABSTRACT

Fixation elements for the socket portions of artificial ball and socket joints are provided which include a self-tapping screw thread, a plurality of cutting teeth and a spherical dome. A spherically-shaped cavity having a radius either approximately equal to or slightly greater than the radius of the spherical dome of the fixation element is reamed into a bony structure. The fixation element is screwed into the cavity using the self-tapping screw thread. The cutting teeth form an aperture in the cavity in advance of the self-tapping thread to aid the thread in cutting into the walls of the cavity. In certain embodiments of the invention, a family of fixation elements is provided having related threads with at least a portion of the thread increasing in size from the smallest to the largest member of the family.

5 Claims, 13 Drawing Figures

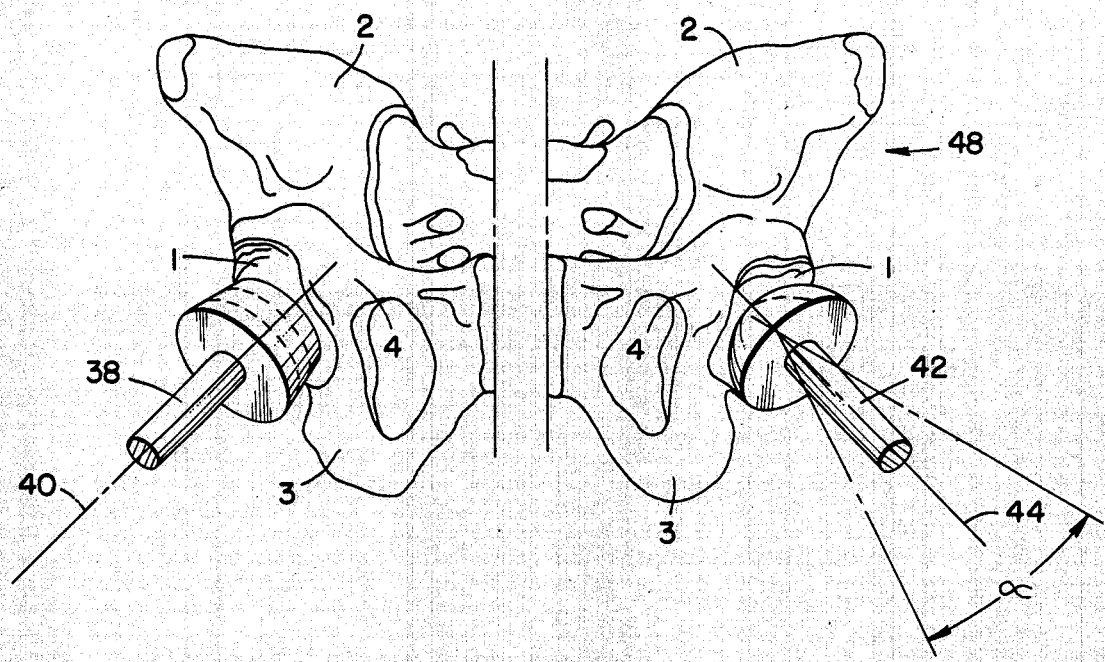
FIG. 1. PRIOR ART
FIG. 2.
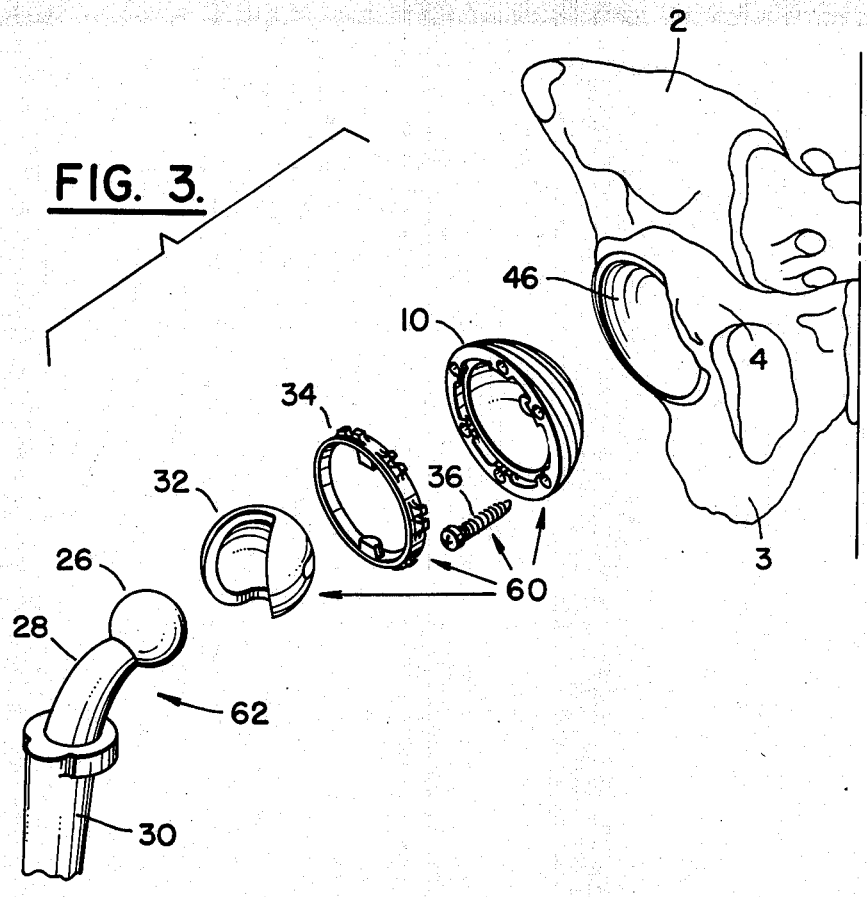
FIG. 3.

FIXATION ELEMENTS FOR ARTIFICIAL JOINTS

BACKGROUND OF THE INVENTION

1. Field of the Invention

This invention relates to artificial joints of the ball and socket type and in particular to fixation elements for use with such joints.

2. Description of the Prior Art

As is well known in the art, artificial hip and shoulder joints conventionally employ ball and socket articulations. The socket portion of the joint is embedded in one bony structure, for example, the pelvis for a hip reconstruction. The ball portion of the joint is attached to another bony structure, for example, the femur for a hip reconstruction.

Over the years, a variety of techniques have been used for embedding the socket portions of these joints in bony structures. Broadly, these techniques fall into two classes: fixations which use cement and fixations which do not use cement. In general, cementless fixations, and especially cementless fixations where metal interfaces directly with bone, have the potential for producing a longer lasting and stronger prosthesis fixation because they do not include cement which can deteriorate with time and which is relatively weak in comparison to metal and bone.

Cementless reconstructions of the hip socket are themselves divided into two classes. In the first class, attachment is achieved by impacting the socket portion of the joint into a prepared cavity in the bony structure. U.S. Pat. No. 3,820,167, issued to K. M. Sivash on June 28, 1974, shows one such impaction construction. In the other class, the socket portion of the joint includes a screw thread on some portion of its outer surface which is used to screw the prosthesis into a prepared cavity in the bony structure. One such screw-in socket made out of ceramic material is the cement free "Autophor" system sold by Osteo AG (Selzach, Switzerland). The present invention relates to such screw-in type sockets.

The screw-in sockets which have been used to date require a three step process for implantation. First, a cavity having the shape of a truncated cone and a cone angle and diameter appropriate to the cone angle and diameter of the threads on the outer surface of the prosthesis and a depth corresponding to the height of the prosthesis is reamed into the bony structure. Next, a thread having a pitch and thread type corresponding to the pitch and thread type on the outer surface of the prosthesis is tapped into the wall of the cavity. Finally, the prosthesis is screwed into the cavity, the threads on the outside of the prosthesis mating with the threads previously tapped into the wall of the cavity.

This implantation procedure has numerous disadvantages, which, as described below, the present invention overcomes. First, and most importantly, the procedure results in the removal of a relatively large amount of bone from the bony structure because the bone's natural shape at the place where the reaming is done is generally spherical, not conical. For example, for hip reconstructions, the cotyloid cavity (also known as the acetabulum), even for severely deformed joints, is generally spherical in shape. To ream a truncated cone out of a sphere requires the removal of a substantial amount of bone, which bone, once removed, obviously cannot be replaced.

Along the same lines, the process of reaming a truncated cone into a spherical cavity in a bony structure runs the risk of puncturing through the bony structure, especially in the areas where large amounts of bone must be removed to change the spherical contour into the desired conical contour. For example, as shown in FIG. 1, the reaming of a conical cavity into cotyloid cavity 1 can result in penetration through to the internal surface of one or more of the ilium 2, ischium 3 or os pubis 4 bones. In particular, in the region of the fossa acetabuli at the bottom of the cotyloid cavity, the ischium and os pubis bones are especially susceptible to penetration during conical reaming because these bones are thinnest in this region.

In addition to the problems caused by bone removal, the currently used procedure also suffers from the disadvantage that the conical reaming must be performed precisely both to insure a tight fit between the prosthesis and the wall of the cavity and because the axis used for reaming defines the final orientation of the socket portion of the prosthesis with respect to the ball portion. Correction of misdirected reaming has generally involved re-reaming the cavity using a larger diameter reamer and then either using a larger socket or employing cement to retain the original socket in the now oversized cavity. Re-reaming is obviously undesirable since it involves the removal of more bone and an enhanced risk of penetration of the bony structure, as well as increasing the time the patient spends under anesthesia.

The prior screw-type prostheses also suffered from the disadvantage of limited options if a secure fixation was not achieved when the socket was screwed into the prepared cavity in the bony structure. Such an insecure fixation could result from the bony structure being composed of especially soft or porous bone. In such a case, the required level of fixation was generally achieved by the use of cement or, in some cases, by re-reaming and retapping the cavity at a larger diameter in the hope of reaching sufficiently strong bone to provide the required level of fixation.

In addition to the foregoing, the use of three separate steps—reaming, tapping and screwing-in—made implantation of prior screw-in type sockets a relatively lengthy procedure in comparison with, for example, the implantation of impaction type prostheses.

SUMMARY OF THE INVENTION

In view of the foregoing problems with prior screw-in type sockets, it is an object of the present invention to provide a screw-in type socket whose implantation is faster, easier and safer than previously used screw-in type sockets.

More particularly, it is an object of the present invention to provide a screw-in type socket wherein a spherically-shaped cavity, rather than a truncated coneshaped cavity, is reamed into a bony structure. Such a spherically-shaped cavity corresponds more closely to the anatomy of the patient's own socket and thus minimizes the amount of bone which needs to be removed and reduces the chances that the reaming process will result in penetration through the bony structure. In addition, spherical reaming does not require a precise orientation of the reaming axis with respect to the patient's anatomy, as required in conical reaming.

It is a further object of the invention to provide a screw-in type socket which is self-tapping so that a separate tapping step need not be performed during implantation of the socket. Such self-tapping both reduces the amount of time needed to implant the prosthesis and results in a stronger prosthesis because the bone chips formed during tapping remain with the prosthesis where they can serve as nuclei for regenerative bone growth, rather than being removed from the thread as occurs when a separate tap is used.

It is an additional object of the invention to provide a set or family of screw-in type sockets of varying sizes, the members of the set being related so that for a given spherical ream, sockets of increasing size, having related threads, can be sequentially screwed into the bony structure until a sufficiently secure fixation is achieved.

It is another object of the invention to provide a screw-in type socket which has an overall outer configuration which allows the socket to be screwed into a spherically-shaped cavity without leaving substantial gaps between the cavity and the socket and without bottoming out against any part of the cavity prior to essentially full insertion of the socket into the cavity.

In order to achieve these and other objects, the invention, in accordance with one of its aspects, provides apparatus for fixation of the socket portion of a ball and socket joint in a bony structure comprising a body having an outer surface which includes a leading portion having one or more cutting teeth for forming an aperture in the bony structure and a trailing portion having a self-tapping screw thread, and means associated with the body for removably connecting the body to driving means for rotating the apparatus to form the aperture in the bony structure by means of the one or more cutting teeth and to affix the apparatus to the bony structure by means of the self-tapping screw thread.

In accordance with another of its aspects, the invention provides apparatus for fixation of the socket portion of a ball and socket joint within a spherically-reamed cavity in a bony structure comprising a body having an outer surface which includes a leading portion in the form of a spherical dome and a trailing portion having a self-tapping screw thread, the radius of said dome being either approximately equal to or less than the radius of said spherically-reamed cavity, and means associated with the body for removably connecting the body to driving means for rotating the apparatus to affix the apparatus to the bony structure by means of the self-tapping screw thread.

In accordance with an additional aspect, the invention provides apparatus for fixation of the socket portion of a ball and socket joint to a bony structure comprising a set of fixation elements of different sizes, each of said elements including a body having an outer surface which includes a leading portion having one or more cutting teeth for forming an aperture in the bony structure and a trailing portion having a self-tapping screw thread, and means associated with the body for removably connecting the body to driving means for rotating the apparatus to form the aperture in the bony structure by means of the one or more cutting teeth and to affix the apparatus to the bony structure by means of the self-tapping screw thread, the pitch of the screw thread on each of the elements in the set being the same and at least a portion of the screw thread increasing in diameter from the smallest to the largest element in the set.

In accordance with a further aspect, the invention provides apparatus for fixation of the socket portion of a ball and socket joint within a spherically-reamed cavity in a bony structure comprising a set of fixation elements of different sizes, each of said elements including a body having an outer surface which includes a leading portion in the form of a spherical dome and a trailing portion having a self-tapping screw thread, the radius of said dome being either approximately equal to or less than the radius of said spherically-reamed cavity, and means associated with the body for removably connecting the body to driving means for rotating the apparatus to affix the apparatus to the bony structure by means of the self-tapping screw thread, the pitch of the screw thread on each of the elements in the set being the same and at least a portion of the screw thread increasing in diameter from the smallest to the largest element in the set.

In accordance with a still further aspect, the invention provides a method for affixing the socket portion of a ball and socket joint to a bony structure comprising the steps of: (a) preparing a cavity in the bony structure using a spherically-shaped reamer; and (b) threading a fixation element for the socket portion into the prepared cavity without first tapping a thread into the walls of said cavity, said fixation element having a self-tapping conical thread on its outside surface which taps a conical thread into the spherically-reamed walls of the cavity as the fixation element is threaded in.

In accordance with a further additional aspect, the invention provides a method for implanting a fixation element for the socket of a ball and socket joint in the body comprising the steps of: (a) preparing a cavity in a bony structure for receiving the fixation element, using a spherically-shaped reamer; (b) based on the size of the prepared cavity, selecting a first fixation element for insertion in the cavity, said fixation element having a self-tapping thread on its outside surface; (c) threading the selected fixation element into the prepared cavity by means of the self-tapping thread; (d) determining whether the degree of fixation of the fixation element appears to be sufficient or insufficient to structurally support the element within the cavity during post-operative use of the joint; and (e) for a degree of fixation which appears to be insufficient, removing the first fixation element from the cavity and replacing it with a second fixation element, without re-reaming the cavity, said second fixation element having a self-tapping screw thread on its outer surface, said screw thread being of the same pitch as the screw thread on the first fixation element and having a portion which is of a greater diameter than the largest diameter of the screw thread on the first fixation element.

In the description of the preferred embodiments which appears below, a construction is shown wherein the socket portion of the artificial joint is composed of a number of detachable elements, i.e., a socket bearing for receiving the ball portion of the joint, a retaining ring and a separate fixation element for attachment to bone. It is to be understood that the term "fixation element" as used herein is intended to describe this construction, as well as unitary constructions wherein one piece serves to affix the element to bone and to receive the ball portion of the joint. Also, in the description which follows, as well as in the drawings, the invention is illustrated with regard to an artificial hip joint. It is to be understood that the invention is equally applicable to other artificial ball and socket joints, such as artificial shoulder joints.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 1 illustrates, for a hip reconstruction, the prior art technique of reaming a conically-shaped cavity to receive the socket portion of an artificial ball and socket joint.

FIG. 2 illustrates the technique of the present invention wherein a spherically-reamed cavity, rather than a conically-reamed cavity, is prepared.

FIG. 3 is an exploded view of the components of a ball and socket joint constructed in accordance with a preferred embodiment of the present invention.

DESCRIPTION OF THE PREFERRED EMBODIMENTS

Figure 4:
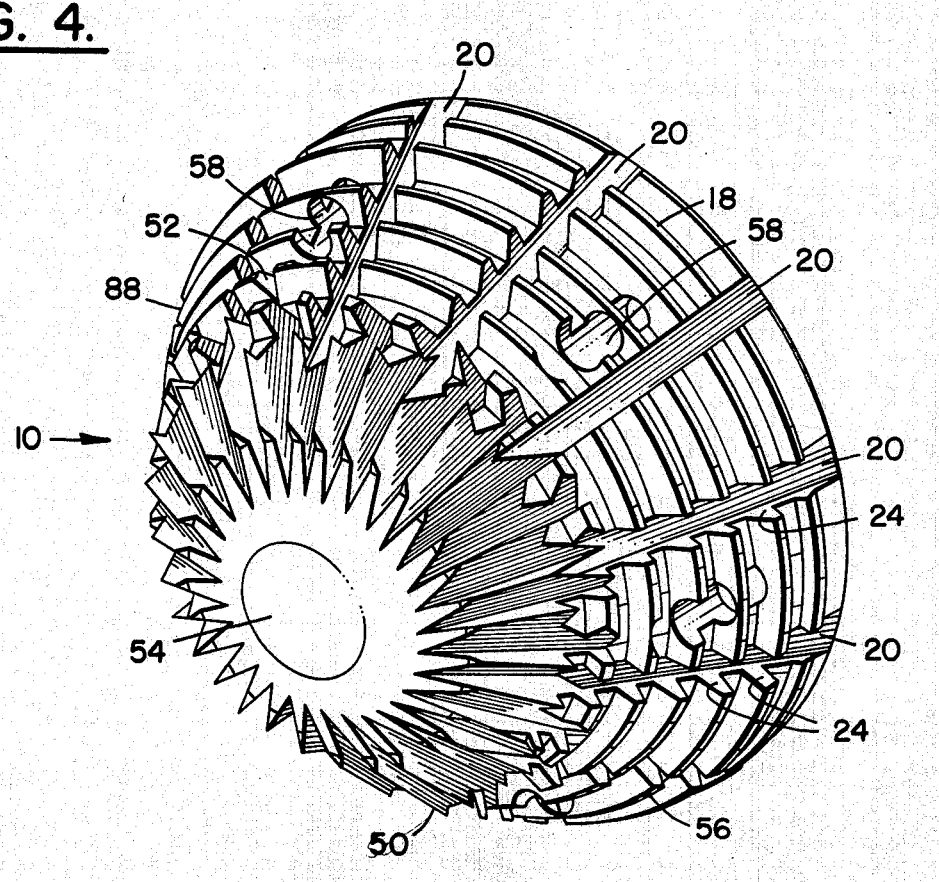
FIG. 4 is a perspective view of the outside surface of a fixation element for the socket portion of an artificial ball and socket joint constructed in accordance with the present invention.

As discussed above, the present invention relates to improved fixation elements for the socket portions of artificial ball and socket joints and improved methods for implanting such joints.

In overview, fixation element 10 includes body 88 having outer surface 56 which includes spherical dome 54 at its leading end 16, self-tapping thread 18 at its trailing end 12, and a set of cutting teeth 50 interposed between spherical dome 54 and self-tapping thread 18. A set or family of fixation elements of different sizes, but with related thread configurations, is provided to the surgeon (see FIGS. 8-9 and Tables 1-2 below).

The surgeon prepares cavity 46 in the bone in which the socket is to be embedded using spherical reamer 42. He selects a first fixation element from the set of fixation elements and attaches it to driver 22. He then inserts the fixation element into cavity 46 by gradually advancing forward and backward rotations of driver 22 to cause self-tapping thread 18 to cut a thread into the walls of cavity 46. If the degree of fixation of element 10 appears to be sufficient to structurally retain the element in cavity 46 during post-operative use of the joint, implantation is complete and the surgeon detaches driver 22 from fixation element 10 and continues with the remainder of the overall surgical procedure.

If the degree of fixation appears not to be sufficient to structurally retain the fixation element in cavity 46, the surgeon rotates driver 22 in the opposite direction to remove fixation element 10 from cavity 46. Driver 22 is then detached from fixation element 10 and a second, larger fixation element is selected from the family of fixation elements and attached to driver 22. This second fixation element is inserted into cavity 46 in the same manner as the first element. The process is repeated until a sufficient degree of fixation to provide structural integrity is achieved. If the process is repeated a substantial number of times, cavity 46 may have to be re-reamed to accommodate the significantly larger fixation elements, using a larger spherical reamer 42.

Fixation with the first selected fixation element is most preferred. In many cases, this result can be achieved if the size of the selected element is properly proportioned relative to the size of the reamed cavity taking into account the density of the patient's bone. That is, for relatively low density bone, i.e., soft bone, a somewhat larger fixation element is used than the size used with relatively high density bone, i.e., hard bone. Also, for soft bone, coarser and deeper threads can be used to enhance the probability of a secure fixation with a first selected fixation element.

During insertion, cutting teeth 50 form an aperture in the walls of cavity 46 in advance of self-tapping thread 18. The aperture makes it easier to thread the fixation element into the cavity. When the fixation element has been fully threaded into cavity 46, spherical dome 54 contacts a portion of the wall of cavity 46. For the most preferred fixation, spherical dome 54 has a spherical radius approximately equal to the spherical radius of spherical reamer 42, e.g., within plus or minus a few millimeters, so that the fixation element does not bottom out prior to essentially full insertion of the element into the cavity and so that substantial gaps between the fixation element and the walls of cavity 46 are minimized for full insertion of the element.

Referring now in detail to the various drawings, wherein like reference characters designate like or corresponding parts throughout the several views, there is shown in FIG. 3 an exploded view of an artificial hip joint constructed in accordance with the preferred embodiments of the invention. Femoral portion 62 of the joint includes ball 26 connected by arm 28 to shaft or stem 30. Shaft or stem 30 is fixed to the femur bone at the time of implant surgery.

Socket portion 60 includes fixation element 10, socket bearing member 32 which receives the ball portion of the joint, retaining ring 34 which removably connects the socket bearing member to the body of the fixation element, and one or more bone screws 36. A detailed description of various constructions for socket bearing 32, retaining ring 34 and the relationships between those parts and fixation element 10 can be found in copending U.S. patent application Ser. No. 473,431, filed on Mar. 8, 1983, copending U.S. patent application Ser. No. 553,520, filed simultaneously herewith, which is a continuation-in-part of application Ser. No. 473,431, and copending U.S. patent application Ser. No. 553,518, now U.S. Pat. No. 4,524,467, to Alfred Frederick DeCarlo, Jr., filed simultaneously herewith, all of which patent applications are assigned to the assignee of the present application. The pertinent portions of these patent applications are incorporated herein by reference. As described in those patent applications, socket bearing 32 can be made of metal or plastic, e.g., ultrahigh molecular weight polyethylene (UHMWPE), and retaining ring 34, fixation element 10 and bone screws 36 are normally made of metal which is structurally and biologically suitable for surgical implantation, such as a titanium alloy which contains 6% aluminum and 4% vanadium (see ASTM Spec. No. F136-79).

As described above, installation of the socket portion of the joint requires the preparation of a cavity in the bony structure to which the socket is to be attached. As shown in FIG. 1, the prior art cavities for screw-in type sockets were prepared using a conically shaped reamer, such as reamer 38. The disadvantages of this type of reaming, including the need to precisely align reaming axis 40, have been discussed above. In contrast, as shown in FIG. 2, the cavity for implantation of the socket portion of the joint of the present invention is spherically reamed using spherical reamer 42. With this type of reaming, the surgeon has a greater latitude (illustrated by the angle α in FIG. 2) in selecting reaming axis 44 and adjusting that axis as the reaming takes place. Such latitude allows the surgeon to select a reaming axis which takes advantage of the patient's anatomy so as to minimize the amount of bone removed. Also, as discussed above, spherical reaming is preferred because in most cases it involves less changes in the contours of the patient's natural cavity, again reducing the amount of bone removed. Further, spherical reaming minimizes the chances of penetration through the bony structure, and if penetration does occur, it typically occurs over a smaller area than with conical reaming.

Figure 5:
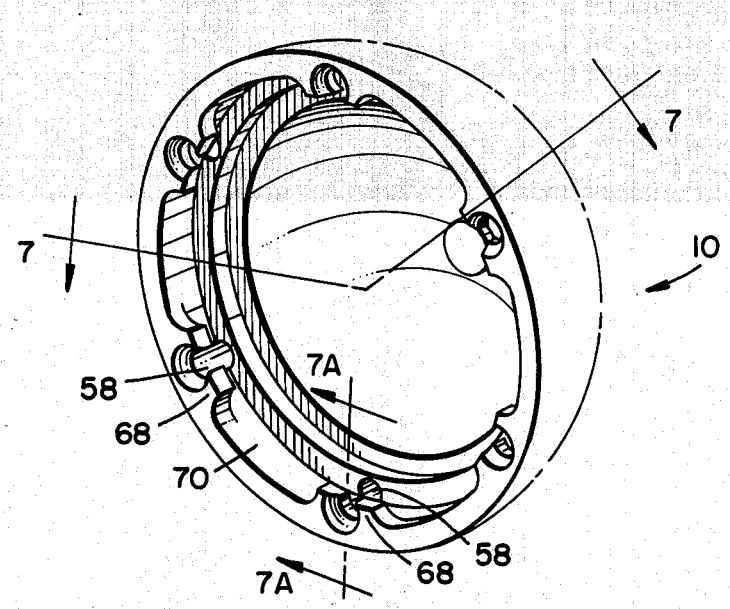
FIG. 5 is a perspective view of the internal structure of the fixation element shown in FIG. 4.
Figure 6:
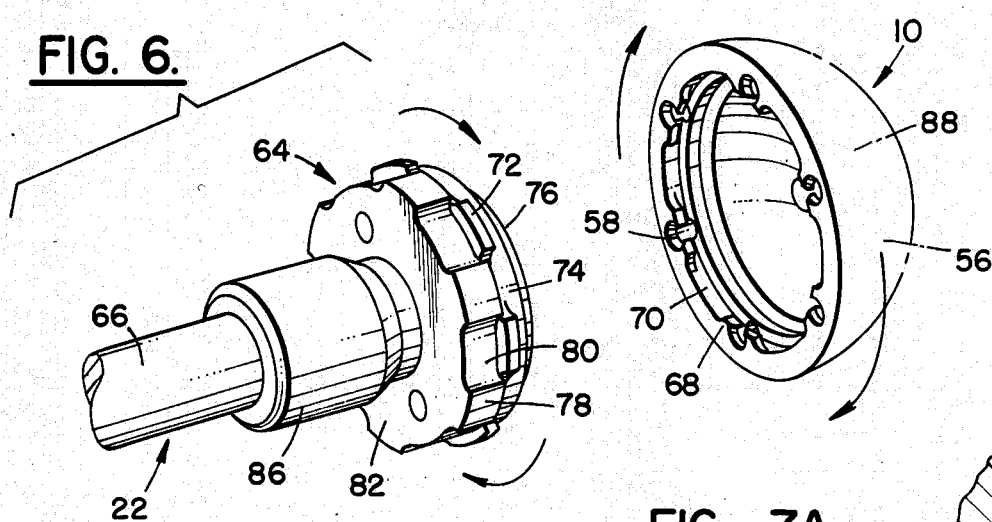
FIG. 6 is a perspective view showing the mating of a driver with the fixation element.
Figure 7A:
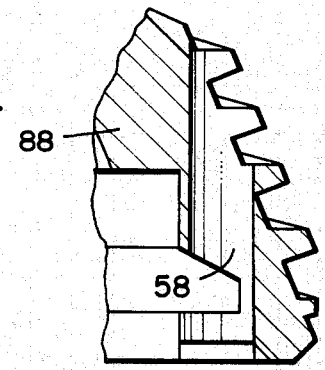
FIG. 7A is an expanded cross-sectional view along lines 7A—7A in FIG. 5.
Figure 7:
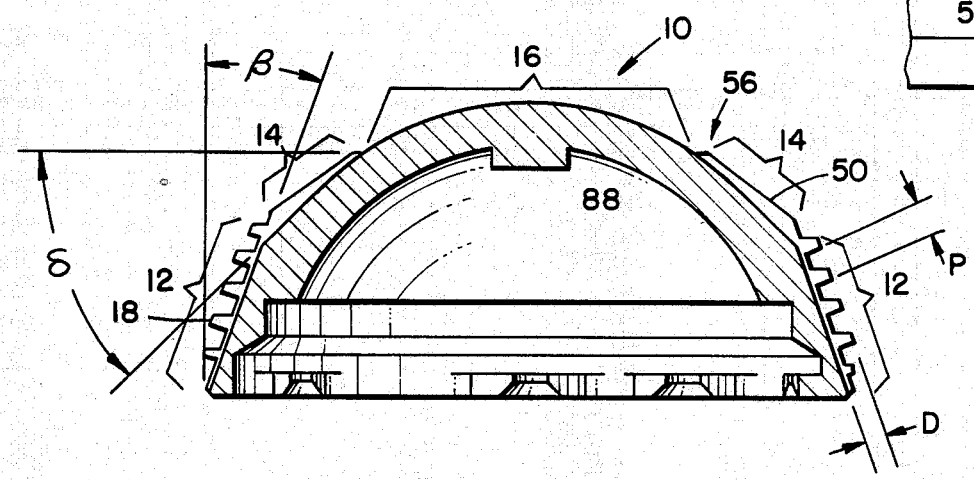
FIG. 7 is a cross-sectional view along lines 7—7 in FIG. 5.

The details of the construction of fixation element 10 are shown in FIGS. 4, 5 and 7. As shown most clearly in FIG. 7, outer surface 56 of fixation element 10 includes leading portion 16, intermediate portion 14 and trailing portion 12. Trailing portion 12 includes self-tapping screw thread 18. Preferably this self-tapping screw thread is a discontinuous conical thread formed, as shown in FIG. 4, by milling a plurality of troughs or slots 20 through conical thread 18. (Note that at its most trailing end, thread 18 becomes a cylindrical thread of constant diameter, rather than a conical thread.) As fixation element 10 is rotated by means of driver 22, the leading edges 24, formed in screw thread 18 by slots 20, tap a thread into the walls of the cavity into which the fixation element is being implanted. The bone chips formed during this tapping process fall into slots 20, as well as any other spaces between fixation element 10 and the walls of the cavity, and serve as nucleation sites for regenerative bone growth about the fixation element. Having the bone chips intimately associated with the thread on the fixation element leads to rapid bone growth in these areas. Such rapid bone growth is important in the healing process and in providing a strong, long lasting prosthetic fixation.

Intermediate portion 14 of outer surface 56 of fixation element 10 includes a plurality of milling or cutting teeth 50. These cutting teeth form an aperture in spherically-reamed cavity 46 whose trailing portion has a cross-sectional diameter corresponding to the leading portion of thread 18. In essence, milling teeth 50 cut away at the spherical surface of cavity 46 and increase the cross-sectional diameter of that cavity to a diameter which allows the leading thread of thread 18 to tap into the walls of cavity 46 more easily.

As shown in FIG. 4, cutting teeth 50 are formed in outer surface 56 of fixation element 10 so that a trailing portion of those teeth overlap with a leading portion of self-tapping thread 18. In this way, some of the threads of thread 18 include contours characteristic of cutting teeth 50, as shown at 52. This makes these threads especially effective in tapping into the walls of cavity 46.

Leading portion 16 of outer surface 56 of fixation element 10 is in the form of a spherical dome. As discussed above, this dome preferably has a radius which is approximately equal to or less than the radius of the spherical reamer used to prepare cavity 46, so that fixation element 10 can be fully inserted into cavity 46, and most preferably, a radius essentially equal to that used to ream cavity 46, so that a minimum of gaps are left between the metal of the prosthesis and the bony material forming the walls of the cavity.

In addition to self-tapping thread 18, cutting teeth 50 and spherical dome 54, outer surface 56 of fixation element 10 also includes screw holes 58 for the passage of one or more bone screws 36. These bone screws serve to prevent fixation element 10 from rotating out of cavity 46 once implantation has been completed. Also, these bone screws can be used to hold retaining ring 34 and its associated socket bearing 32 within fixation element 10, as described in the above referenced co-pending patent applications.

Fixation element 10 is inserted in cavity 46 by means of driver 22. Driver 22 includes head portion 64 and shaft 66 which is connected to a conventional handle (not shown) for rotating the driver. Driver 22 mates with fixation element 10 by means of bayonet lugs 68 and spaces 70.

Figure 12:
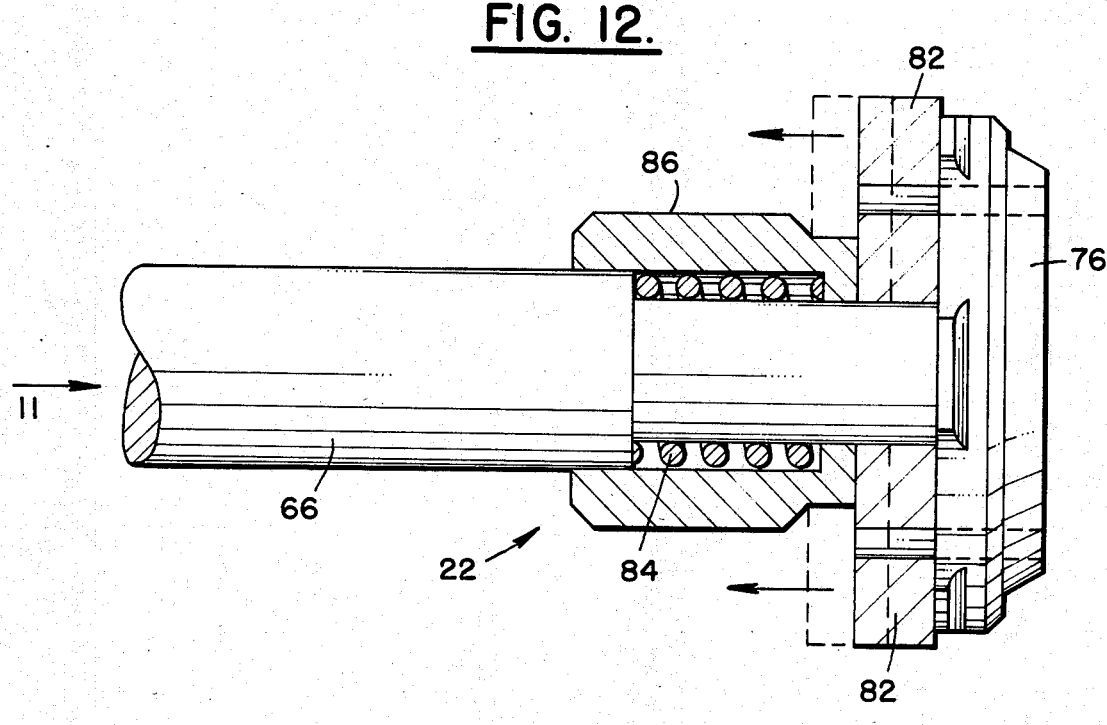
FIG. 12 is a side view, partially in section along lines 12—12 in FIG. 11, of the driver of FIGS. 6 and 11.

Head portion 64 of driver 22 includes two sets of bayonet lugs and spaces sized to mate with bayonet lugs 68 and spaces 70. The first set of spaces 74 and lugs 72 are formed on plate 76 which is rigidly attached to shaft 66. The second set of spaces 80 and lugs 78 are formed on plate 82 which can slide axially along shaft 66, but cannot rotate about that shaft. As shown in FIG. 12, spring 84 biases plate 82 against plate 76. Knurled knob 86 is rigidly attached to plate 82 and is used to move that plate axially away from plate 76 against the biasing force of spring 84.

Driver 22 is mated with fixation element 10 by first inserting lugs 72 on plate 76 into bayonet spaces 70 formed in the fixation element. Bayonet lugs 78 on plate 82 rest on bayonet lugs 68 on fixation element 10 in this configuration. Shaft 66 is then pushed inward against the biasing force of spring 84 until lugs 72 lie inward of lugs 68. Plate 82 remains stationary with respect to fixation element 10 during this motion because of the engagement of lugs 78 with lugs 68. Shaft 66 is then rotated, in either direction, through an angle corresponding to one half the angular spacing between lugs, e.g., 30 for six bayonet lugs and spaces. Bayonet lugs 72 ride under bayonet lugs 68 during this motion, and bayonet lugs 78 ride over bayonet lugs 68 during this motion. When bayonet lugs 78 reach bayonet spaces 70, spring 84 moves plate 82 towards fixation element 10 and into engagement with plate 76. Fixation element 10 is now locked onto driver 22 by the interference of lugs 72 under lugs 68 and the interference of lugs 78 against the sides of lugs 68 which prevents rotation of head portion 64 to a position where lugs 72 are no longer in engagement with lugs 68. The engagement of lugs 78 with the edges of lugs 68 also serves to transfer rotational torque from driver 22 to fixation element 10 during insertion of that element into cavity 46.

To detach driver 22 from fixation element 10, plate 82 is moved away from fixation element 10 against the biasing force of spring 84, by means of knurled knob 86, until lugs 78 are out of interference with lugs 68. Shaft 66 is then rotated, in either direction, through one half the angle corresponding to the spacing between bayonet lugs until lugs 72 on plate 76 are in alignment with bayonet spaces 70 on fixation element 10. Driver 22 can then be moved away from fixation element 10, completing the detachment process.

It should be noted that bayonet lugs 68 and spaces 70 not only serve for the attachment of driver 22 to fixation element 10, but also serve to hold retaining ring 34 and its associated socket bearing 32 within fixation element 10 in the completed prosthesis (see FIG. 3 and the above-referenced patent applications).

In accordance with the most preferred embodiments of the invention, the surgeon is supplied with a set or family of fixation elements, having related self-tapping threads 18, which increase in size from the smallest to the largest element in the set, so that a suitably high degree of fixation can be achieved by using successively larger fixation elements in the family. Preferably, all members of the family have the same thread pitch so that larger fixation elements are capable of mating with the thread cut into the walls of cavity 46 by smaller fixation elements. Also, in proceeding from the smallest to the largest element in the family, at least a portion of the screw thread increases in diameter so that ever tighter fits can be achieved.

In addition to thread pitch and size, other parameters characteristic of the fixation elements can either change or be held constant from one member of the family to the next. Examples of such parameters include the thread depth, the conical angle, when a conical thread is used, the radius of spherical dome 54, when a spherical dome is used, and the slope of milling teeth 50, when milling teeth are used. By means of these types of parameters, a set of fixation elements can be divided into sub-families or subsets, such as sub-families related to a particular reaming radius for spherical reamer 42.

Figure 8:
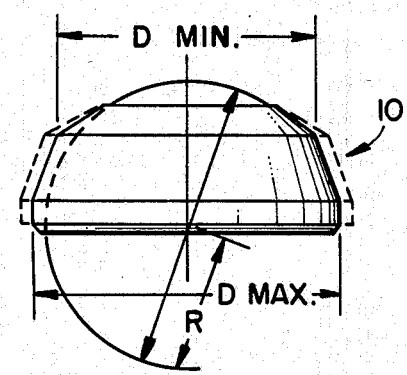
FIG. 8 illustrates the geometric relationships between the members of a family of fixation elements prepared in accordance with the present invention.
Figure 9:
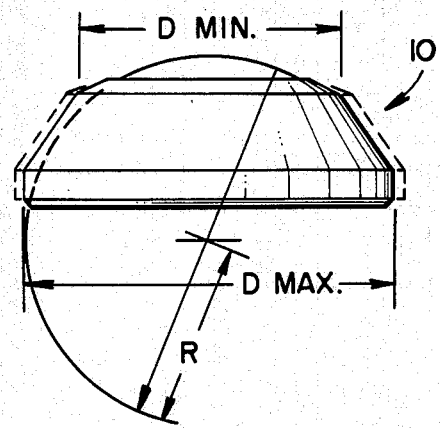
FIG. 9 illustrates the same geometric relationships as in FIG. 8, but for a larger family of fixation elements.
Figure 10:
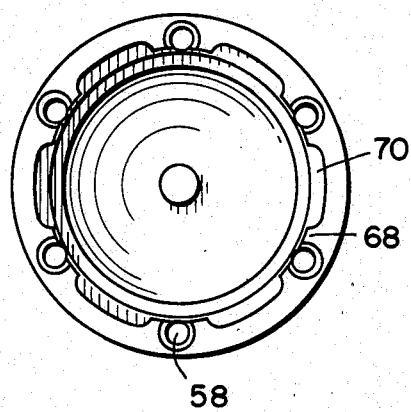
FIG. 10 is a plan view of the trailing face of the fixation element. In combination with FIG. 11, this figure shows in detail how the driver of FIG. 6 mates with the fixation element.
Figure 11:
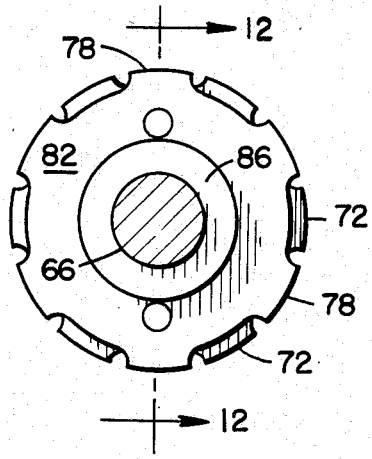
FIG. 11 is a view from behind of the head portion of the driver.

The characteristics of a family and three sub-families of fixation elements suitable for use with adult artificial hip joints are described in Table 1 and FIGS. 8-9. The definitions of the various parameters listed in Table 1 are shown in FIGS. 7-9. FIGS. 8 and 9 correspond to sub-families 1 and 3, respectively, in Table 1. The solid lines in these figures represent the smallest member of each sub-family, and the dotted lines, the largest member.

The overall family includes seven fixation elements. All members of the family have the same thread pitch, i.e, approximately 2 millimeters, so that any member of the family can be threaded into the thread cut by another member of the family. The maximum outside thread diameter increases from the smallest to the largest member of the family by a constant increment of approximately 2.0 millimeters.

The seven elements are divided into three sub-families, each of the sub-families, for convenience of manufacture, having a constant dome radius, conical angle and milling teeth angle. Three spherical reamers 42 may be used with the overall family, each reamer having a spherical reaming head of a radius equal to the dome radius of one of the sub-families. In most cases, a secure fixation will be achieved using the members of only one sub-family. Since the sub-families have a constant conical angle, minimal disruption of the thread produced by smaller members of the sub-family will occur when a larger member is threaded into cavity 46. Also, since each member of each sub-family has a spherical dome radius equal to the reaming radius used to prepare cavity 46, each member can be fully inserted into the cavity with a minimum of gaps between the prosthesis and the walls of the cavity.

In some cases, it may be necessary to use members of the next largest sub-family in order to achieve the requisite security of fixation. Because of the constant pitch between sub-families, and the fact that the minimum outside thread diameter of the smallest member of the next largest sub-family is in all cases smaller than the maximum outside thread diameter of the largest element of the next smaller sub-family, such a transition between sub-families can be made, at least in the first instance, without re-reaming. Early bottoming out may occur for such a transition to the next largest sub-family without re-reaming since the dome radius of the next largest sub-family will be greater than the reaming radius used to prepare cavity 46. However, because of the cutting action of teeth 50, the relatively small changes in dome radius between sub-families, and the small angular extent of dome 54, a satisfactory level of fixation will be achieved in most cases notwithstanding the difference between reaming radius and dome radius. Of course, re-reaming, if necessary, can be performed. Also, as an alternative, all family members can be given a dome radius corresponding to the smallest reaming radius. This will eliminate early bottoming out due to transitions between sub-families, but at the expense of leaving gaps in some cases between the prosthesis and the cavity when larger reamers have been used.

It should be noted that the heights of the fixation elements remain essentially constant both within and between sub-families, notwithstanding the fact that the diameters of the elements are increasing (compare FIG. 8 which illustrates the height/width ratio for sub-family 1 with FIG. 9 which illustrates the same ratio for sub-family 3). This constancy is built into the family to correspond to the natural constancy of human cotyloid cavities, which in general vary more in diameter than depth.

As an alternative to using only three reamers with the seven fixation elements of Table 1, a particular reamer can be employed for each fixation element. The last column of Table 1 includes a list of preferred reamer spherical diameters designed to enhance the probability of a secure fixation of the fixation element on the first insertion. These reamer sizes, all of which are commercially available, have been selected so that the thread penetration of the fixation element's conical thread into the patient's bone on average equals the depth of the tread. Because of this criteria, in some cases the dome radius is slightly larger than the reaming radius. As discussed above, in most cases this will not result in substantial early bottoming out of the fixation element in the spherically-reamed cavity because of the cutting action of teeth 50, the small differences between the reaming radius and the dome radius, and the small angular extent of dome 54. Of course, if desired, each member of the overall family can be given its own dome radius corresponding to its preferred reaming radius listed in Table 1.

Numerous modifications and variations of the present invention are possible in light of the above teachings. For example, a variety of families of fixation elements different from that shown in Table 1 and illustrated in FIGS. 8-9 can be used with the invention, both for artificial hip joints and for other artificial joints using a ball and socket construction, such as shoulder joints.

The parameters of one such alternate family of fixation elements for use with hip joints is given in Table 2. This family, which includes six rather than seven members, has a thread pitch of approximately 3.0 millimeters and a thread depth for most members of the family of also approximately 3.0 millimeters. The remaining parameters of this family are similar to those given in Table 1.

Besides variations in the families of fixation elements used, various drivers and ways of removably coupling such drivers to the fixation elements can be used with the invention. Similarly, various modifications can be made to the internal components of the fixation element, i.e., the part or parts which receive the ball portion of the joint, without departing from the concept of the present invention.

TABLE 1

| Sub-Family | Pitch (P) | Thread Depth (D) | Conical Angle ($\beta$) | Max. Outside Thread Diameter ($D_{max}$) | Min. Outside Thread Diameter ($D_{min}$) | Dome Radius (R) | Milling Teeth Angle ($\delta$) | Preferred Reamer Spherical Diameter |
|---|---|---|---|---|---|---|---|---|
| 1 | 2.0 mm | 1.5 mm | 20° | 52 mm | 43 mm | 24 mm | 35° | 48.0 mm |
|   | 2.0 mm | 2.3 mm | 20° | 54 mm | 46 mm | 24 mm | 35° | 50.8 mm |
| 2 | 2.0 mm | 2.3 mm | 30° | 56 mm | 42 mm | 27 mm | 25° | 50.8 mm |
|   | 2.0 mm | 2.3 mm | 30° | 58 mm | 45.5 mm | 27 mm | 25° | 54.0 mm |
|   | 2.0 mm | 2.3 mm | 30° | 60 mm | 49 mm | 27 mm | 25° | 57.2 mm |
| 3 | 2.0 mm | 2.3 mm | 35° | 62 mm | 44 mm | 31 mm | 20° | 58.7 mm |
|   | 2.0 mm | 2.3 mm | 35° | 64 mm | 48 mm | 31 mm | 20° | 61.9 mm |

TABLE 2

| Sub-Family | Pitch (P) | Thread Depth (D) | Conical Angle ($\beta$) | Max. Outside Thread Diameter ($D_{max}$) | Min. Outside Thread Diameter ($D_{min}$) | Dome Radius (R) | Milling Teeth Angle ($\delta$) | Preferred Reamer Spherical Diameter |
|---|---|---|---|---|---|---|---|---|
| 1 | 3.0 mm | 2.3 mm | 20° | 54 mm | 46 mm | 24 mm | 35° | 50.8 mm |
| 2 | 3.0 mm | 3.0 mm | 30° | 56 mm | 42 mm | 27 mm | 25° | 48.0 mm |
|   | 3.0 mm | 3.0 mm | 30° | 58 mm | 45.5 mm | 27 mm | 25° | 50.8 mm |
|   | 3.0 mm | 3.0 mm | 30° | 60 mm | 49 mm | 27 mm | 25° | 54.0 mm |
| 3 | 3.0 mm | 3.0 mm | 35° | 62 mm | 44 mm | 31 mm | 20° | 57.2 mm |
|   | 3.0 mm | 3.0 mm | 35° | 64 mm | 48 mm | 31 mm | 20° | 58.7 mm |

What is claimed is:

1. Apparatus for fixation of the socket portion of a ball and socket joint in a bony structure comprising a cup-shaped body which is screwed into a spherically-shaped cavity formed in the bony structure, said body having an outer surface which includes a leading portion having a plurality of cutting teeth for forming an aperture in the bony structure, said cutting teeth covering the full circumference of said leading portion and being oriented to cut into bone and produce bone chips when turned in the direction in which the cup-shaped body is screwed into the spherically-shaped cavity, and a trailing portion having a self-tapping screw thread, said self-tapping screw thread covering the full circumference of said trailing portion and being oriented to cut into bone and produce bone chips when turned in the direction in which the cup-shaped body is screwed into the spherically-shaped cavity, and means associated with the body for removably connecting the body to driving means for rotating the apparatus to form the aperture in the bony structure by means of the plurality of cutting teeth and to affix the apparatus to the bony structure by means of the self-tapping screw thread, the bone chips produced by the cutting of bone by the cutting teeth and the self-tapping screw thread remaining in the region between the cup-shaped body and the spherically-shaped cavity.

2. The apparatus of claim 1 wherein the self-tapping screw thread comprises a discontinuous conical thread.

3. The apparatus of claim 1 wherein the connecting means also removably connects the body to a socket bearing member which receives the ball portion of the ball and socket joint.

4. The apparatus of claim 3 wherein the connecting means comprises bayonet spaces and lugs.

5. The apparatus of claim 1 wherein a leading portion of the self-tapping screw thread and a trailing portion of the one or more cutting teeth overlap so that a portion of the screw thread includes contours characteristic of the cutting teeth.

* * * * *